United States Patent [19]

Tazi et al.

[11] Patent Number: 5,126,124
[45] Date of Patent: Jun. 30, 1992

[54] HAIR SPRAY RESIN COMPOSITION

[75] Inventors: Mohammed Tazi, Marietta, Ga.; Stephen L. Shernov, Long Valley, N.J.; Edward W. Walls, Jr., Cranford, N.J.; Robert B. Login, Oakland, N.J.

[73] Assignee: ISP Investments Inc., Wilmington, Del.

[21] Appl. No.: 681,273

[22] Filed: Apr. 8, 1991

[51] Int. Cl.$^5$ .................................. A61K 7/11
[52] U.S. Cl. ........................... 424/47; 424/71; 424/78.08; 424/78.24
[58] Field of Search .................... 424/47, 71

[56] References Cited

U.S. PATENT DOCUMENTS

| | | | |
|---|---|---|---|
| 4,192,862 | 3/1980 | Pengilly | 424/47 |
| 4,223,009 | 9/1980 | Chakrabarti | 424/47 |
| 4,874,604 | 10/1989 | Sramek | 424/47 |
| 4,996,045 | 2/1991 | Leighton | 424/71 |

*Primary Examiner*—Thurman K. Page
*Assistant Examiner*—William E. Benston, Jr.
*Attorney, Agent, or Firm*—Walter Katz; Marilyn J. Maue; Joshua J. Ward

[57] ABSTRACT

A hair spray resin compositon is provided herein which is capable of delivering a fine finishing mist at a high resin solids level. The composition is substantially moisture resistant, provides a stiff resin film having excellent hair holding power, and has a relatively low concentration of volatile organic compounds therein. The composition of the invention attains its unique attributes by including a predetermined blend of at least two hair spray resins, one being a relatively high molecular weight resin, and the other resin having a relatively low molecular weight. The latter resin is present in the composition in a substantially greater proportion than the higher molecular weight resin.

19 Claims, No Drawings

HAIR SPRAY RESIN COMPOSITION

BACKGROUND OF THE INVENTION

1. Field of the Invention

This invention relates to hair spray resin compositions, and more particularly, to such compositions which contain a low amount of volatile organic compounds.

2. Description of the Prior Art

Present hair spray compositions, both pump spray and aerosol spray formulations, are described in detail in U.S. Pat. Nos. 3,145,147; 4,223,009; and 4,521,402. These compositions generally perform effectively in providing most of the properties considered desirable for hair preparation, including fine spray patterns, prolonged curl retention under humid conditions, good holding power, ease of removability, and resistance to build-up. However, these and other pump formulations available in the art contain a considerable amount of alcohol which is a volatile organic compound (VOC). Aerosol hair spray formulations also require hydrocarbons or other propellants which add to the VOC content of the composition. Recent state legislation, moreover, has required that hair spray compositions have a lower VOC level than is presently found in commercial hairspray compositions. More particularly, it is now necessary that such compositions contain VOC materials at a weight level of no more than 80% of the composition.

Accordingly, it is an object of the present invention to provide new hair spray compositions which meet VOC standards while retaining the effective properties of presently available compositions for hair preparation and treatment.

Another object of the invention is to provide hair spray resin compositions capable of providing a fine finishing mist at a high resin solids level and which is substantially moisture resistant, also forms a stiff resin film on the hair of the user, and provides a good hold and curl retention, and which composition has a substantially reduced VOC level, particularly a lower alcohol concentration in pump formulations, and, a low level of alcohol and propellant components in aerosol-based formulations.

These and other objects and features of the invention will be made apparent from the following more particular description thereof.

SUMMARY OF THE INVENTION

A hair spray resin composition is provided herein which is capable of delivering a fine finishing mist at a high resin solids level. The composition is substantially moisture resistant, provides a stiff resin film having excellent hair holding power, and has a relatively low concentration of volatile organic compounds therein. The composition of the invention attains its unique attributes by including a predetermined blend of at least two hair spray resins, one being a relatively high molecular weight resin, and the other resin having a relatively low molecular weight. The latter resin is present in the composition in a substantially greater proportion than the higher molecular weight resin.

The pump hair spray resin composition of the invention consists essentially of:

(a) a high molecular weight resin having a molecular weight between about 50,000 and 1,000,000, in an amount of about 0.5-10% by weight of the composition;

(b) a low molecular resin having a molecular weight of less than 50,000, in an amount of about 0.5-20% by weight.

The molecular weight ratio of (a) to (b) being about 4.5 to 10:1, the weight ratio of (a) to (b) being about 1:2 to 1:50, and the total weight amount of (a)+(b) present being about 10-25%;

(c) water in an amount of about 15-50% by weight; and (d) alcohol in an amount of about 30-70% by weight.

In the form of an aerosol, the hair spray resin composition of the invention consists essentially of about 50-80% by weight of the concentrate defined above and about 20-50% by weight of a suitable propellant.

In the preferred form of the invention, (a) is a terpolymer derived from the polymerization of vinyl caprolactam, vinylpyrrolidone and an ammonium derivative monomer having from 6 to 12 carbon atoms selected from the group consisting of dialkyl dialkenyl ammonium halide and a dialkylamino alkyl acrylate or methacrylate, having a molecular weight of about 150,000; and (b) is polyvinylpyrrolidone (PVP) having a molecular weight of about 15,000 (K-15), in a weight ratio of a:b of about 1.6, and wherein the total weight of (a) and (b) is about 13%.

DETAILED DESCRIPTION OF THE INVENTION

The pump hair spray composition of the present invention comprises:

| Component | % by wt. Suitable | Preferred | Optimum |
|---|---|---|---|
| (a) High molecular weight resin | MW 50,000–1,000,000 | 60,000–250,000 | 70,000–150,000 |
| Concentration (% by weight) | 0.5–10 | 2–8 | 5 |
| (b) Low molecular weight resin | MW less than 50,000 | 20,000 or less | 15,000 |
| Concentration (% by weight) | 0.5–20 | 5–15 | 8 |
| (c) Water (% by weight) | 15–50 | 20–40 | 37 |
| (d) Alcohol (% by weight) | 30–70 | 40–60 | 50 | where: the MW ratio of (a):(b) is about 4.5–10:1; the weight ratio of (a):(b) is about 1:2–1:50; and the total weight concentration of (a) + (b) is about 10–25%.

The aerosol hair spray composition comprises:

| | | | |
|---|---|---|---|
| (1) Hair spray concentrate | 50–80 | 60–70 | 65 |
| (2) Propellant | 20–50 | 30–40 | 35 |

Suitable aerosol propellants include aliphatic hydrocarbons, e.g. butane, propane; $CO_2$, nitrous oxide, dimethylether and difluoroethane, and mixtures thereof.

Suitable high molecular weight resins used in the resin blend of the invention include;

1. Gaffix ® VC-713 (GAF Chemicals Corporation) which is a terpolymer derived from the polymerization of vinyl caprolactam, vinylpyrrolidone and an ammonium derivative monomer having from 6–12 carbon atoms selected from the group consisting of dialkyl dialkenyl ammonium halide and a dialkylamino alkyl acrylate or methacrylate (see U.S. Pat. No. 4,521,404).

A typical molecular weight of this resin is about 150,000. The commercial product is available as a ethanolic solution having a 37% solids level.

2. Gantrez® SP-215 (GAF Chemicals Corporation) is the ethyl half-ester of a linear copolymer of methyl-vinylether and maleic anhydride having a molecular weight of about 70,000.

3. Gantrez® ES-225 (GAF Chemicals Corporation) is the ethyl half-ester of a linear copolymer of methyl-vinyl ether and maleic anhydride having a molecular weight of 978,000.

4. Gantrez® ES-425 (GAF Chemicals Corporation) is the butyl half-ester of a linear copolymer of methyl-vinyl ether and maleic anhydride having a molecular weight of 1,000,000.

5. Resin 1212 (GAF Chemicals Corporation) is a terpolymer derived from the polymerization of vinyl acetate, mono-n-butyl maleate and isobornyl acrylate (see U.S. Pat. No. 4,689,373), having a molecular weight of about 250,000.

EXAMPLE 1

The following composition of the invention was prepared and tested for effectiveness as a pump hair spray product.

| Component | Wt. % |
|---|---|
| Gaffix® VC-713 resin (provided as a 37% active solution in ethanol) MW 150,000 | 5.0 of resin |
| PVP (K-15) (GAF) MW 15,000 | 8.0 |
| Aminomethylpropanol | 0.1 |
| Ethanol | 60.0 |
| Water | 26.9 |
| | 100.0 |

The above formulation was a one-phase system upon testing as a pump hair spray, it was observed that the spray patterns developed were fine, broad and dry.

EXAMPLE 2

| Component | Wt. % |
|---|---|
| Gantrez® SP-215 resin (provided as a 50% active solution in ethanol) MW 70,000 | 10.0 of resin |
| PVP (K-15) MW 15,000 | 8.0 |
| Aminomethylpropanol | 0.22 |
| Ethanol | 45.0 |
| Water | 36.78 |
| | 100.0 |

The above formulation was a one phase system. Upon testing as a pump hair spray it was observed that the spray patterns developed were fine, broad and dry.

EXAMPLE 3

The composition of Example 2 was prepared using Resin 1212 in place of Gantrez® SP-215 with similar results in use as a pump spray formulation.

COMPARATIVE EXAMPLES

PVP (K-30), PVP (K-60) and PVP (K-90) were substituted for PVP (K-15) in the compositions of Examples 1-3. The formulations thus produced exhibited poor viscosity and gave very narrow, streamy and wet spray patterns.

PROCEDURE FOR PREPARING COMPOSITIONS OF INVENTION

A. Pump Spray

The pump hair spray compositions of the invention were prepared by first providing an ethanol solution including the neutralizing agent and dissolving the higher molecular weight resin therein. Then the requisite amount of water was added followed by gradually sifting in the lower molecular weight resin. The composition then was packaged into a plastic bottle fitted with a suitable pump actuator such as the Calmar Mark II pump actuator.

B. Aerosol Compositions

The aerosol hair spray resin compositions of the invention were prepared from 65% by weight of the concentrate of the pump spray formulation of Example 1 and a 35% by weight of dimethylether propellant.

While the invention has been described with particular reference to certain embodiments thereof, it will be understood that changes and modifications may be made which are within the skill of the art. Accordingly, it is intended to be bound only by the following claims, in which:

What is claimed is:

1. A hair spray composition comprising:
  (a) a resin having a molecular weight between about 50,000 and 1,000,000, wherein said resin is selected from a terpolymer derived from the polymerization of vinyl caprolactam, vinylpyrrolidone and an ammonium derivative monomer having from 6-12 carbon atoms selected from the group consisting of dialkyl dialkenyl ammonium halide and a dialkylamino alkyl acrylate or methacrylate, an ethyl half-ester of a linear copolymer of methyl vinyl ether and maleic anhydride, and a terpolymer derived from the polymerization of vinyl acetate, n-butyl maleate and isobornyl acrylate, in an amount of about 0.5-10% by weight of the composition,
  (b) a resin having a molecular weight of less than 50,000, in an amount of about 0.5-20% by weight of the composition, the molecular weight ratio of (a) to (b) being about 4.5:1 to 10:1, the weight ratio of (a) to (b) being about 1:2 to 1:50, and
  the total amount of (a)+(b) present being about 10 to 25%;
  (c) water in an amount of about 15-50% by weight; and
  (d) alcohol in an amount of about 30-70% by weight, of the composition.

2. A hair spray composition according to claim 1 wherein resin (a) has a molecular weight of about 60,000 to 250,000.

3. A hair spray composition according to claim 1 wherein resin (a) has a molecular weight of about 70,000 to 150,000.

4. A hair spray composition according to claim 1 wherein resin (a) is present in a concentration of about 2-8% by weight.

5. A hair spray composition according to claim 1 wherein resin (b) has a molecular weight of about 20,000 or less.

6. A hair spray composition according to claim 1 wherein resin (b) has a molecular weight of about 15,000.

7. A hair spray composition according to claim 1 wherein resin (b) is present in a concentration of about 5-15% by weight.

8. A hair spray composition according to claim 1 wherein water (c) is present in the amount of about 20-40% by weight of the composition.

9. A hair spray composition according to claim 1 wherein alcohol is present in the amount of about 40-60% by weight of the composition.

10. An aerosol hair spray composition comprising about 50-80% by weight of the concentrate of claim 1 and about 20-50% by weight of a propellant.

11. A composition according to claim 10 which comprises about 60-70% by weight of the concentrate of claim 1 and about 30-40% by weight of a propellant.

12. A hair spray composition according to claim 1 wherein resin (b) is polyvinylpyrrolidone.

13. A hair spray composition according to claim 12 wherein said resin (b) has a molecular weight of about 15,000.

14. A hair spray composition according to claim 1 which also includes a neutralizing agent.

15. A composition according to claim 14 wherein said neutralizing agent is aminomethylpropanol.

16. A composition according to claim 1 which comprises about 5% by weight of resin (a), about 8% by weight of resin (b), about 37% by weight of water, and about 50% by weight of alcohol.

17. A composition according to claim 1 wherein said alcohol is ethanol.

18. An aerosol hair spray composition which comprises about 65% by weight of the concentrate of claim 1 and about 35% by weight of a propellant.

19. A composition according to claim 10 wherein said propellant is selected from aliphatic hydrocarbons, nitrous oxide, $CO_2$, dimethylether and difluoroethane, and mixtures thereof.

* * * * *